United States Patent
Abels et al.

(10) Patent No.: US 7,396,230 B2
(45) Date of Patent: Jul. 8, 2008

(54) MOLAR ORTHODONTIC BRACKETS HAVING A HINGED BRACKET COVER

(76) Inventors: Norbert Abels, Alleestrasse 30a, 66424 Homburg (DE); Claus-H. Backes, St. Wendeler Strasse 45, 66113 Saarbrücken (DE)

( * ) Notice: Subject to any disclaimer, the term of this patent is extended or adjusted under 35 U.S.C. 154(b) by 0 days.

(21) Appl. No.: 10/836,074

(22) Filed: Apr. 30, 2004

(65) Prior Publication Data

US 2005/0244775 A1 Nov. 3, 2005

(51) Int. Cl.
*A61C 3/00* (2006.01)
(52) U.S. Cl. .......................................................... 433/11
(58) Field of Classification Search ...................... 433/2, 433/8, 10; 206/63.5
See application file for complete search history.

(56) References Cited

U.S. PATENT DOCUMENTS

| | | | |
|---|---|---|---|
| 1,976,141 A | 10/1934 | Richardson | 29/160.6 |
| 3,303,565 A | 2/1967 | Newman | 32/14 |
| 3,391,461 A | 7/1968 | Johnson | 43/14 |
| 3,748,740 A * | 7/1973 | Wildman | 433/11 |
| 3,969,821 A | 7/1976 | Lee, Jr. et al. | 32/14 A |
| 4,103,423 A | 8/1978 | Kessel | 32/14 A |
| 4,492,573 A | 1/1985 | Hanson | 433/11 |
| 4,547,153 A | 10/1985 | Taylor | 433/11 |
| 4,597,739 A | 7/1986 | Rosenberg | 433/16 |
| 4,614,497 A * | 9/1986 | Kurz | 433/8 |
| 4,655,708 A * | 4/1987 | Fujita | 433/10 |
| 4,669,980 A | 6/1987 | Degnan | 433/8 |
| 4,712,999 A | 12/1987 | Rosenberg | 433/8 |
| 4,799,882 A | 1/1989 | Kesling | 433/8 |
| 4,820,151 A * | 4/1989 | Pospisil | 433/17 |
| 4,867,678 A | 9/1989 | Parker | 433/8 |
| 4,878,840 A | 11/1989 | Reynolds | 433/9 |
| 4,927,360 A | 5/1990 | Pospisil | 433/8 |
| 4,927,362 A | 5/1990 | Snead | 433/17 |
| 5,174,754 A | 12/1992 | Meritt | 433/8 |
| 5,221,202 A * | 6/1993 | James | 433/9 |
| 5,269,681 A | 12/1993 | Degnan | 433/11 |
| 5,282,743 A | 2/1994 | Miura | 433/8 |
| 5,299,934 A | 4/1994 | Suyama | 433/8 |
| 5,474,445 A | 12/1995 | Voudouris | 435/10 |
| 5,516,284 A | 5/1996 | Wildman | 433/10 |
| 5,562,444 A | 10/1996 | Heiser et al. | 433/11 |

(Continued)

FOREIGN PATENT DOCUMENTS

DE 10035992 A1 2/2000

(Continued)

*Primary Examiner*—Melba Bumgarner
(74) *Attorney, Agent, or Firm*—Workman Nydegger

(57) ABSTRACT

Self-ligating molar orthodontic brackets are used to terminate an arch wire during an orthodontic procedure. The molar orthodontic brackets include a bracket base, an arch wire slot in the bracket base oriented toward the occlusal edge of a tooth during use, and ligation cover selectively movable between an open, non-ligating position and a closed, ligating position relative to the arch wire slot. The ligation cover can be hingedly attached to the base by an integral film hinge such that the molar bracket may be injection molded as a single piece of plastic. The self-ligating nature of the molar brackets and the orientation of the arch wire slots make insertion of an arch wire into the arch wire slots of the molar brackets much simpler compared to tube brackets.

17 Claims, 10 Drawing Sheets

U.S. PATENT DOCUMENTS

| | | | |
|---|---|---|---|
| 5,630,715 A | 5/1997 | Voudouris | 433/8 |
| 5,630,716 A | 5/1997 | Hanson | 433/14 |
| 5,685,711 A | 11/1997 | Hanson | 433/11 |
| 5,711,666 A | 1/1998 | Hanson | 433/11 |
| 5,857,849 A * | 1/1999 | Kurz | 433/10 |
| 5,913,680 A * | 6/1999 | Voudouris | 433/10 |
| 6,042,373 A | 3/2000 | Hermann | 433/13 |
| 6,053,729 A * | 4/2000 | Brehm et al. | 433/9 |
| 6,071,119 A | 6/2000 | Christoff et al. | 433/14 |
| 6,089,861 A * | 7/2000 | Kelly et al. | 433/9 |
| 6,347,939 B2 | 2/2002 | Abels | 433/10 |
| 6,361,314 B1 * | 3/2002 | Garton, Jr. | 433/8 |
| 6,428,314 B1 * | 8/2002 | Jones et al. | 433/17 |
| 6,659,766 B2 | 12/2003 | Abels et al. | |
| 6,709,268 B2 * | 3/2004 | Pospisil et al. | 433/17 |
| 6,843,370 B2 * | 1/2005 | Tuneberg | 206/369 |
| 6,960,080 B2 | 11/2005 | Abels et al. | |
| 2001/0029007 A1 | 10/2001 | Abels | 433/10 |
| 2002/0034715 A1 | 3/2002 | Hanson | 433/11 |

FOREIGN PATENT DOCUMENTS

| | | |
|---|---|---|
| DE | 19856794 A1 | 6/2000 |
| EP | 0 317 098 A2 | 5/1989 |
| EP | 0 351 177 A1 | 1/1990 |
| EP | 0 453 250 A1 | 10/1991 |
| EP | 0 624 354 A2 | 11/1994 |
| EP | 1234549 A1 | 8/2002 |
| WO | WO 9107925 | 11/1993 |

* cited by examiner

MOLAR ORTHODONTIC BRACKETS HAVING A HINGED BRACKET COVER

BACKGROUND OF THE INVENTION

1. The Field of the Invention

The present invention relates to orthodontic brackets. More specifically, it relates to molar orthodontic brackets that terminate a set of orthodontic brackets that hold an arch wire.

2. The Relevant Technology

Orthodontics is a specialized field of dentistry that involves the application of mechanical forces to urge poorly positioned, or crooked, teeth into correct alignment and orientation. Orthodontic procedures can be used for cosmetic enhancement of teeth, as well as medically necessary movement of teeth to correct underbites or overbites. For example, orthodontic treatment can improve the patient's occlusion, or enhanced spatial matching of corresponding teeth.

The most common form of orthodontic treatment involves the use of orthodontic brackets and wires, which together are commonly referred to as "braces." Orthodontic brackets, more particularly the orthodontic bases, are small slotted bodies configured for direct attachment to the patient's teeth or, alternatively, for attachment to bands which are, in turn, cemented or otherwise secured around the teeth. Once the brackets are affixed to the patient's teeth, such as by means of glue or cement, a curved arch wire is inserted into the slot of each bracket. The arch wire acts as a template or track to guide movement of the teeth into proper alignment. End sections of the arch wire are typically captured within tiny appliances known as tube brackets or terminal brackets, which are affixed to the patient's molars.

The arch wire holder of existing terminal brackets is essentially a tunnel through the bracket, open at only the mesial-distal ends. Because the arch wire slot is not open at the labial side of the bracket, it is not possible to insert the wire in the slot by simply placing the arch wire down into the slot. The arch wire must be fed through the side of the bracket. Because of this, the procedure of inserting the arch wire through the tube bracket can be somewhat difficult, especially when it must be performed while inserting the arch wire into the arch wire slots of the other brackets. FIG. 1 illustrates the difficulty of this procedure, which requires the orthodontic practitioner to carefully insert the arch wire 2 into the arch wire tunnel 4, accessible only at the mesial end of terminal bracket 6. Once the arch wire 2 has been fed through the tunnel 4 in the terminal bracket 6, the end of the arch wire 2 may be bent to prevent it from sliding out of the terminal bracket 6. In this way, the terminal bracket acts as an anchor from which the arch wire causes the patient's teeth to move as desired.

It would be an improvement in the art to provide a molar orthodontic bracket that more easily and conveniently accepted and held an arch wire therein. Such a bracket would greatly simplify the procedure of placing the arch wire in the holder of the molar bracket.

BRIEF SUMMARY OF THE INVENTION

As used herein, the term "mesial-distal" refers to a direction along a dental arch running from a tooth surface closest to the middle of the front of the jaw to a tooth surface farthest from the middle of the front of the jaw and the vice versa direction.

As used herein, the term "occlusal-gingival" refers to a direction running from the occlusal edge of the tooth to the gingival edge of the tooth and the vice versa direction.

The molar orthodontic brackets according to the present invention are generally low-cost, simple to manufacture, and compact in construction. Generally, the molar orthodontic brackets of the present invention include a bracket base, a ligation cover, and an arch wire slot for receiving an arch wire. The arch wire slot is disposed in the bracket base and oriented so as to point toward the occlusal surface of the tooth to which it is attached.

The bracket is preferably formed as one single piece, requiring no assembly. This reduces the cost and complexity of manufacture and prevents unwanted separation of the bracket parts. In a preferred embodiment, the inventive orthodontic bracket can be made from a single type of material, more preferably plastic. Although other methods may be used, low cost manufacture is possible by forming the bracket by injection molding.

The brackets of the present invention are self-ligating, i.e., the arch wire is enclosed or otherwise retained between the ligation cover and the bracket base by closing the ligation cover. According to one embodiment, the ligation cover is attached to the bracket base by an integral film hinge, and the cover is selectively rotatable relative to the bracket base between an open, non-ligating position and a closed, ligating position relative to the arch wire slot. The orthodontic bracket preferably includes a latch mechanism that acts to selectively lock the ligation cover to the bracket base in the closed, ligating position. The cover may optionally include a bearing protrusion that extends toward the arch wire slot when the ligation cover is in the closed, ligating position.

The bracket may include a hook formed on the gingival side of the bracket oriented so as to point toward the gingival surface of the tooth to which it is attached. The hook may be configured for securing one end of a class II elastic.

Because the molar bracket is designed for terminating the arch wire, it is beneficial to form at least one of the bracket base or ligation cover in an elongated configuration in the mesial-distal direction, so as to form a bracket that is significantly longer than existing non-molar brackets. At least one of the bracket base or ligation cover has a mesial-distal length that is greater than its incisal-gingival width. The elongated bracket base and/or ligation cover allows the molar bracket to retain a significantly longer length of the arch wire, resulting in a better termination of the arch wire.

It is especially advantageous for the bonding surface or platform of the bracket base to be lengthened in the mesial-distal direction so as to form a bond across a greater width of the molar. Such a bond better withstands strong torque forces that might tend to dislodge the bracket from the molar to which it is bonded.

These and other features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only typical embodiments of the invention and are therefore not to be considered limiting of its scope. The invention will be described and explained with additional specificity and detail through the use of the accompanying drawings in which.

DETAILED DESCRIPTION OF THE PREFERRED EMBODIMENTS

I. Introduction

Figure 1:
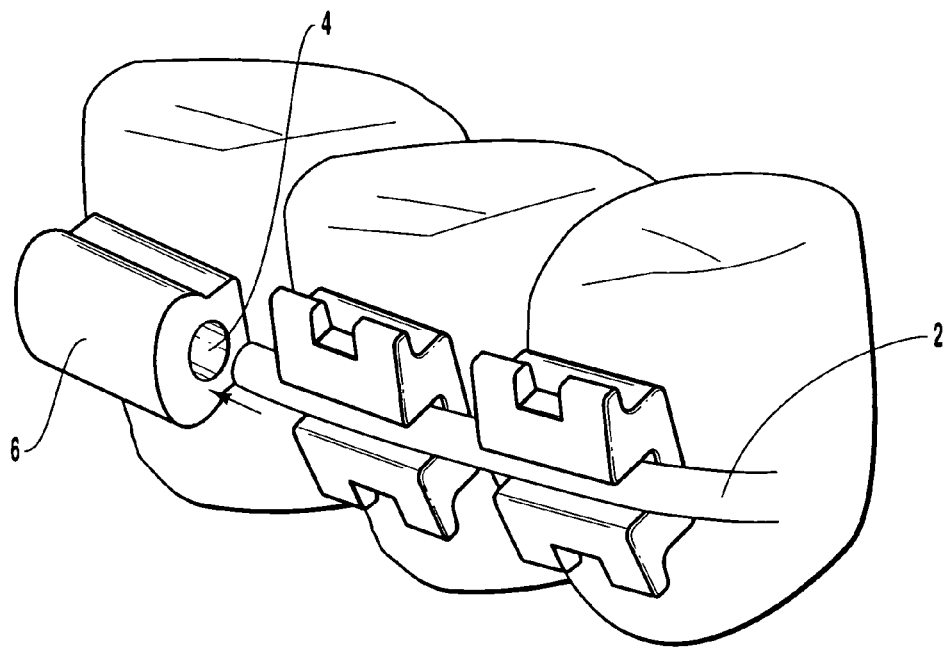
FIG. 1 is a perspective view of a plurality of conventional orthodontic brackets and a terminal tube bracket.

The molar orthodontic brackets of the present invention are designed for placement on a patient's molars for termination of an arch wire. The orthodontic brackets are designed to replace conventional tube brackets to retain the end portions of an arch wire during an orthodontic procedure. The molar brackets are self-ligating, i.e., the arch wire is retained by closing the ligation cover over the base of the bracket. The molar brackets may optionally be configured to additionally accept one or more supplemental ligatures for more securely retaining an arch wire at its termination.

Generally, the orthodontic brackets of the present invention include a bracket base, a ligation cover, and an arch wire slot disposed in the bracket base. In use, the arch wire slot is oriented so as to point towards the occlusal surface of the tooth to which it is attached. This orientation simplifies insertion and removal of the arch wire. In addition, this orientation allows the bracket to reside closer to the gingival margin than the occlusal edge of the tooth. This helps prevent inadvertent biting, damage or dislodgement of the brackets in the event of chewing, biting, or grinding of food using the molars.

The bracket is self-ligating, meaning that the arch wire is retained in the arch wire slot by closing the cover over the base. No ligatures are required to retain the arch wire in the slot. The cover is hingedly attached to the base so as to be selectively movable relative to the bracket base between an open, non-ligating position and a closed, ligating position relative to the arch wire slot. When the cover is in the open position, the arch wire slot is accessible from the incisal side of the bracket, making insertion of the arch wire much easier than feeding it through the tunnel of a tube bracket.

Because the brackets are intended for terminating the arch wire, it is beneficial to form the molar orthodontic brackets in an elongated configuration. In other words, at least one of the bracket base or ligation cover has a mesial-distal length that is greater than its incisal-gingival width. This greater mesial-distal length allows the bracket base and/or ligation cover to retain a significantly longer length of the arch wire than a non-molar self-ligating bracket, thereby resulting in a more effective arch wire termination. The mesial-distal length of at least one of the bracket base or ligation cover is preferably at least about 125% of its incisal-gingival width, more preferably at least about 150% of its incisal-gingival width, and most preferably at least about 200% of its incisal-gingival width. It may also be beneficial to maximize the mesial-distal length of the bonding surface or platform beneath the bracket base in order to increase the length and strength of the bond between the bracket base and the molar surface. This helps prevent dislodging the bracket from the molar as a result of strong torque forces applied by the arch wire to the bracket.

The bracket may include a hook formed on the gingival side of the bracket and oriented so as to point toward the gingival surface of the tooth to which it is attached. The hook may be configured so as to secure one end of a class II elastic.

II. Exemplary Molar Orthodontic Brackets

The following description is directed to exemplary embodiments of the present invention, which invention may be embodied in other various forms.

Figure 2A:
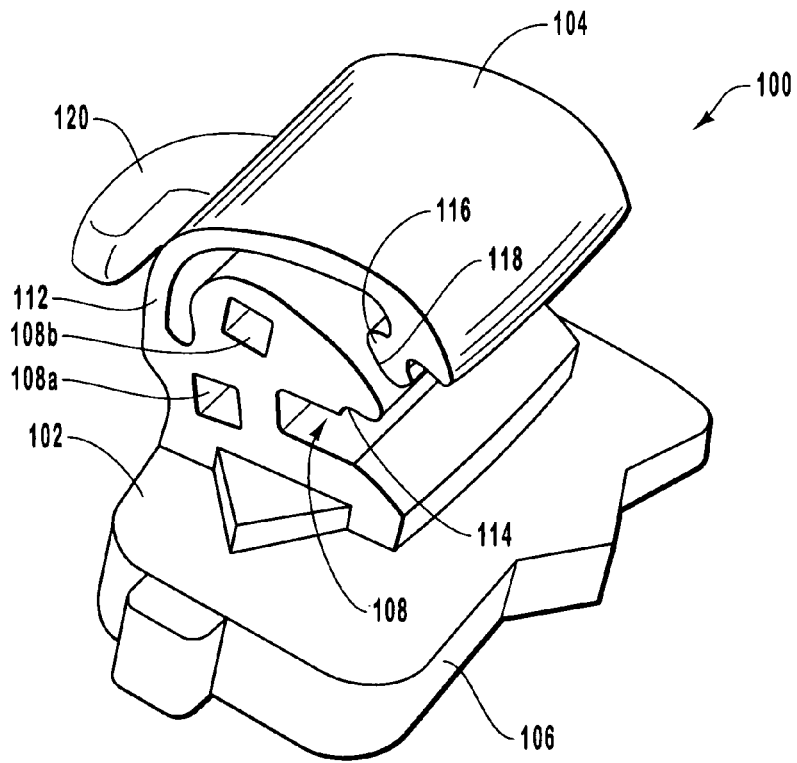
FIGS. 2A-2C illustrate an exemplary molar orthodontic bracket according to the invention.
Figure 2B:
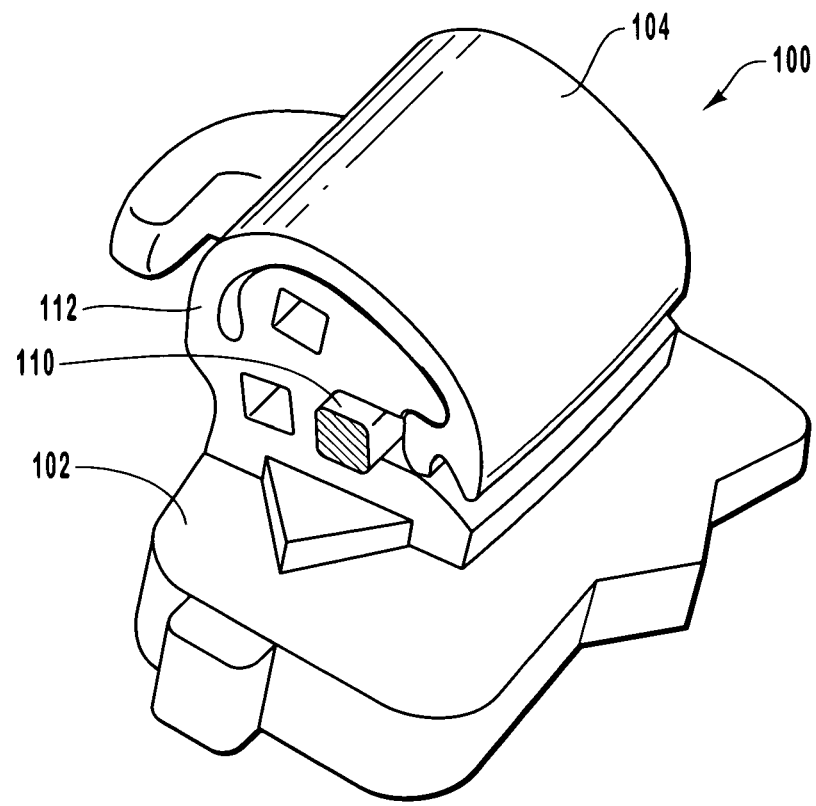
Figure 2C:
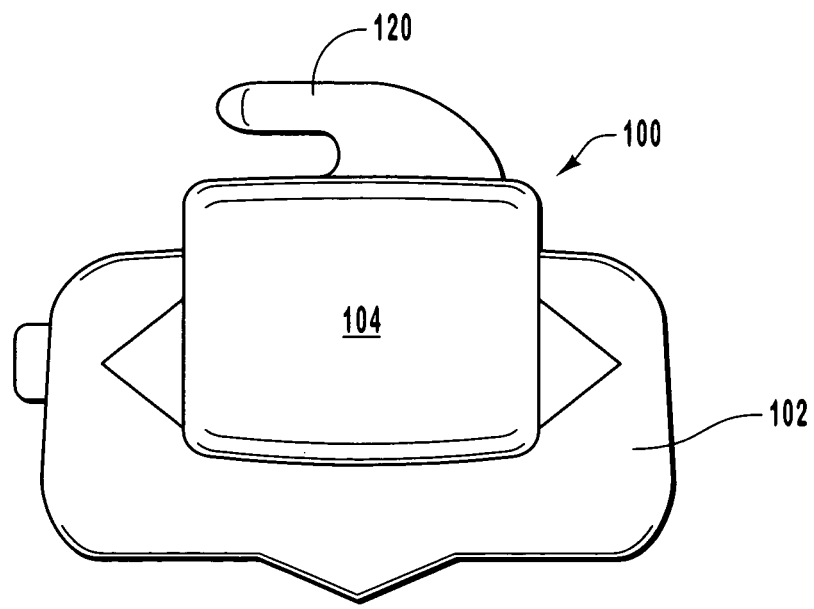

FIGS. 2A-2C illustrate an exemplary embodiment of a molar orthodontic bracket according to the present invention. The bracket 100 is especially configured for placement on the first upper molars, although it may be used on other molars, as desired. The bracket 100 may be manufactured as a single piece of plastic, such as by injection molding. Forming the bracket as a single piece is advantageous because it results in a simple, low cost bracket requiring no assembly. The molar orthodontic bracket 100 includes a bracket base 102 to which a ligation cover 104 is hingedly attached. The bracket base 102 may include an enlarged bonding platform 106, which may include a rough bottom surface for aiding bonding to the labial surface of a patient's molar. The base 102 includes a raised portion wherein is disposed an arch wire slot 108 which serves as a holder for arch wire 110 (FIG. 2B). The arch wire 110 shown with a rectangular cross-section (any other cross section known in the art could be used) is arranged by the orthodontic practitioner inside the slot 108 and serves to correct the teeth in a known manner. The bracket may also include auxiliary tunnels 108a and 108b.

The orthodontic bracket 100 is simple in design and construction. The ligation cover 104 is selectively rotatable relative to the bracket base 102 between an open, non-ligating position and a closed, ligating position relative to the arch wire slot 108. FIG. 2A illustrates the ligation cover 104 in an open, non-ligating position, and FIG. 2B illustrates the ligation cover 104 in a closed, ligating position. FIG. 2C illustrates the bracket 10 from above with the ligation cover in a closed, ligating position. As clearly illustrated in FIG. 2A, the arch wire slot 108 is completely non-occluded when the ligation cover 104 is in the open, non-ligating position shown in FIG. 2A. Apart from the arch wire slot 108 being completely non-occluded, no portion of the ligation cover 104 remains directly over the arch wire slot 108 when in the open position shown in FIG. 2A.

The bracket base 102 is preferably attached to the ligation cover 104 by an elongate film hinge 112. Elongate film hinge 112 is defined by a localized region of reduced cross-sectional thickness. Although the ligation cover 104 is attached to the bracket base 102 by an elongate film hinge 112 in the illustrated embodiment, other types of hinges, for example, multiple film hinges, or a mechanical hinge (e.g., a pin hinge), could be used. Various hinges that could be used are disclosed in U.S. Pat. No. 6,607,383 and U.S. application Ser. Nos. 09/914,737, and 09/953,400, each of which is hereby incorporated by reference.

The elongate film hinge 112 is sufficiently thick so as to be durable, but sufficiently thin so as to flex and bend as the ligation cover 104 is closed. When in the closed, ligating position, the ligation cover 104 covers at least a portion of the arch wire slot 108, retaining the arch wire 110 within the slot 108. In addition, when in the closed position, the ligation cover 104 forms a uniform, smooth surface along the labial surface of the orthodontic bracket 100, which offers a significant advantage in comfort to the patient (see FIGS. 2B and 2C). In addition, the uniform and smooth surface of the ligation cover 104 prevents food particles and other potential contaminants from becoming lodged in or on the bracket.

To selectively lock the ligation cover 104 to the bracket base 102 in the closed, ligating position, the orthodontic bracket may include a latch mechanism. One embodiment of the latch mechanism includes an angled keyway 114 disposed mesially-distally along a side of the bracket base 102 opposite to where the ligation cover 104 is attached to the bracket base and a corresponding locking tongue 116 disposed mesially-distally along the same opposite end of the ligation cover 104. When latched, the latch mechanism locks the ligation cover 104 to the bracket base 102 as seen in FIG. 2B.

Furthermore, a bearing protrusion 118 may be provided at the inside and near the end of ligation cover 104. Bearing protrusion 118 extends toward the arch wire slot 108 when the ligation cover 104 is in the closed, ligating position (see FIG. 2B), functioning like a tube bracket so as to retain the arch wire 110 in the slot 108.

To facilitate use of class II elastics, the bracket may further include a hook 120. Hook 120 is configured to secure one end of a class II elastic. In a typical class II elastic treatment, the other end of the elastic is secured to a bracket bonded to the canine of the opposite dental arch.

Figure 3A:
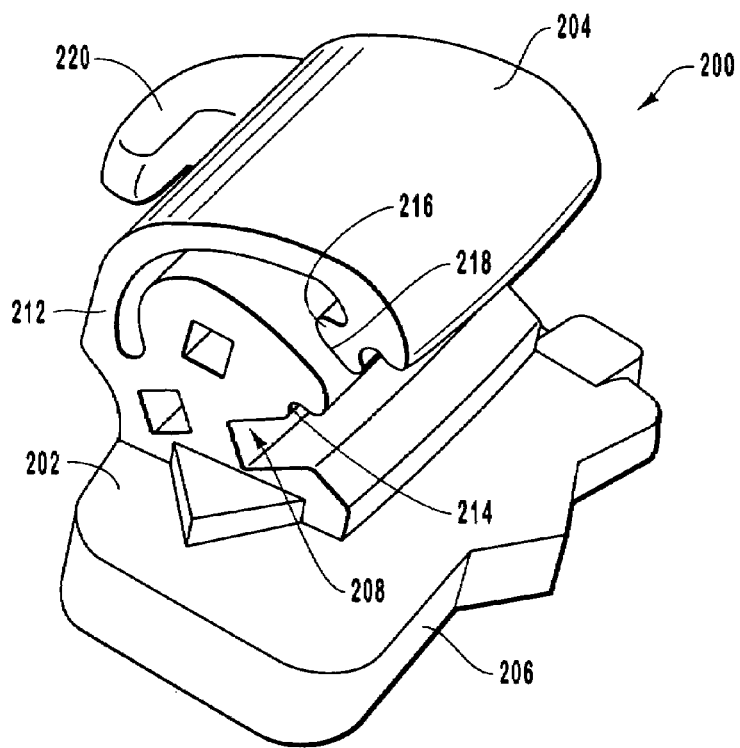
FIGS. 3A-3C illustrate another exemplary molar orthodontic bracket according to the invention.
Figure 3B:
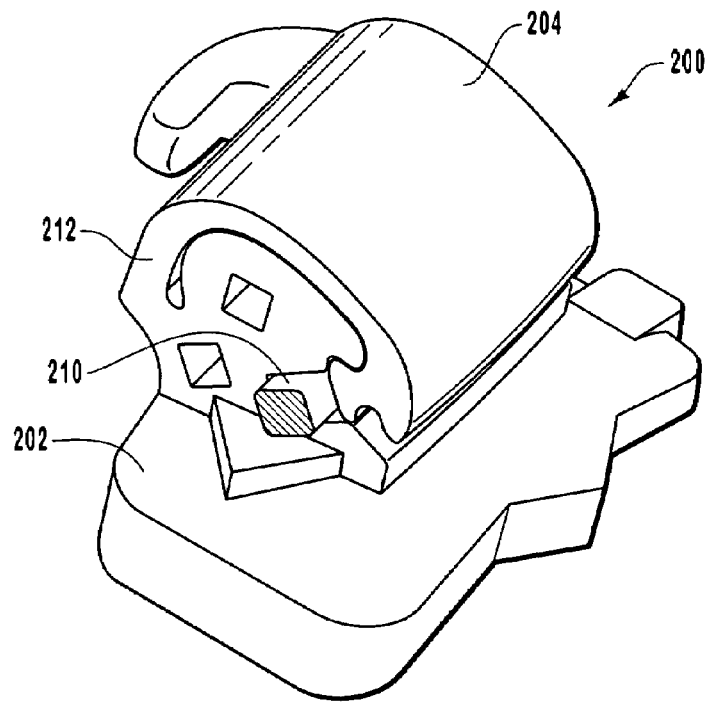
Figure 3C:
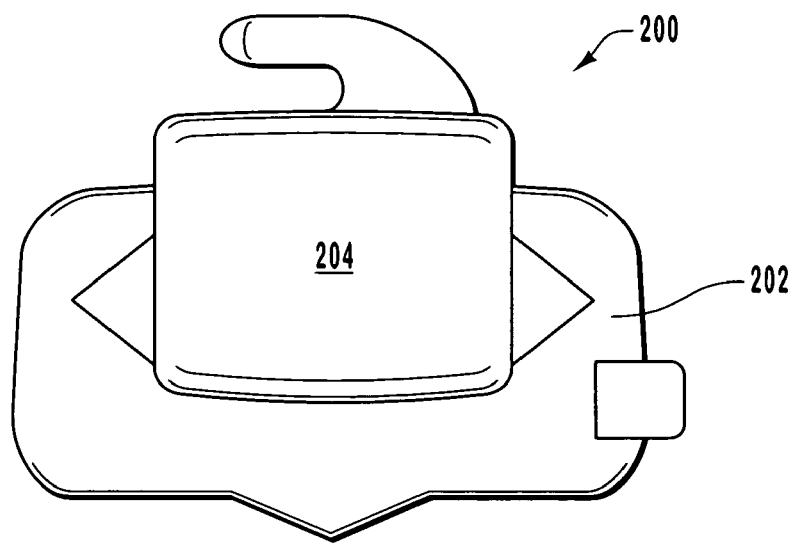

FIGS. 3A-3C illustrate another exemplary embodiment of a molar orthodontic bracket according to the present invention. The bracket 200 is especially configured for placement on the first lower molars, although it may be used on other molars, as desired. The bracket 200 includes a bracket base 202, a ligation cover 204, a bonding platform 206, an arch wire slot 208, an arch wire 210, an elongate film hinge 212, an angled keyway 214, a locking tongue 216, a bearing protrusion 218, and a hook 220. The orientation of the arch wire slot 208 within the base 202 is angled in toward the tooth. This orientation facilitates easier insertion of the arch wire 210 when the bracket 200 is bonded to a first lower molar.

Figure 4A:
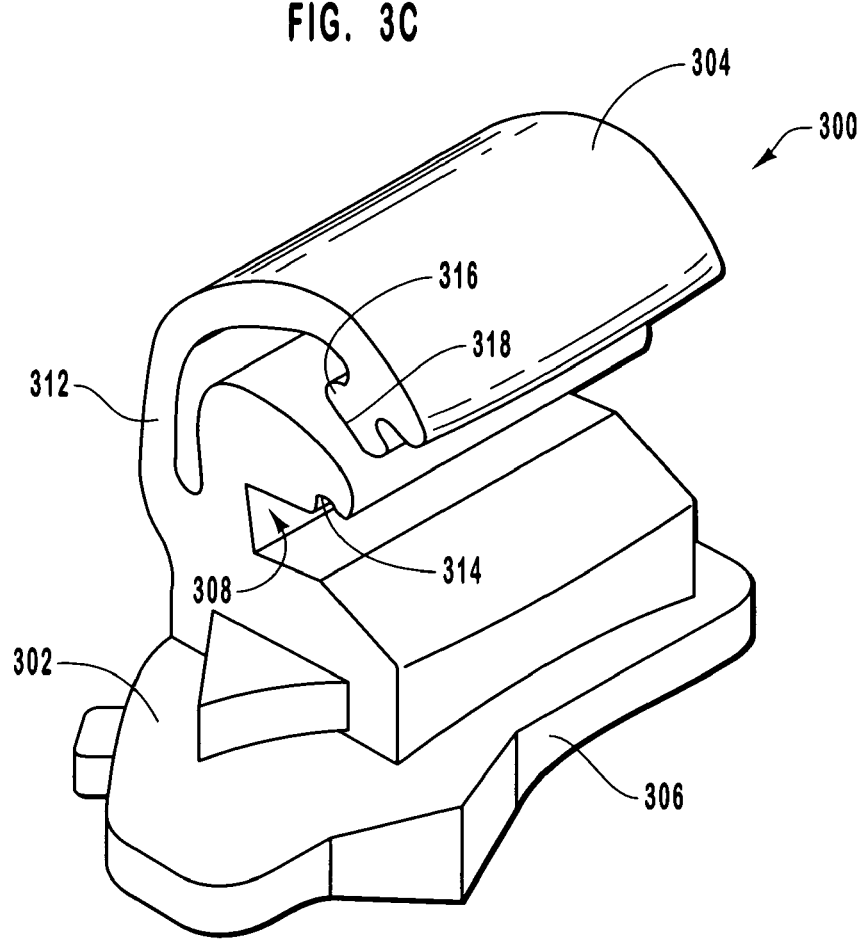
FIGS. 4A-4C illustrate yet another alternative exemplary molar orthodontic bracket according to the invention.
Figure 4B:
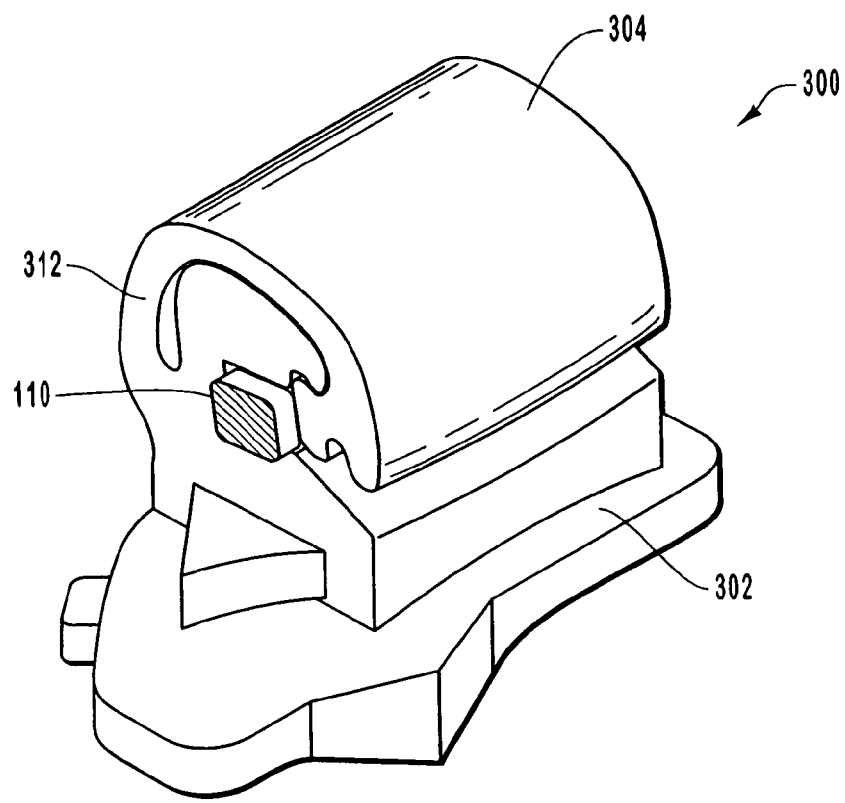
Figure 4C:
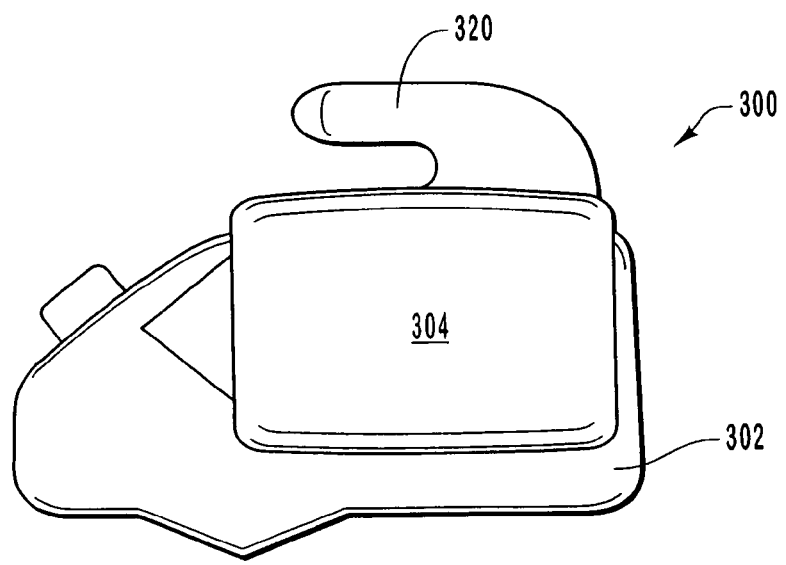

FIGS. 4A-4C illustrate another exemplary embodiment of a molar orthodontic bracket according to the present invention. The bracket 300 is especially configured for placement on the second upper molars, although it may be used on other molars, as desired. The bracket 300 includes a bracket base 302, a ligation cover 304, a bonding platform 306, an arch wire slot 308, an elongate film hinge 312, an angled keyway 314, a locking tongue 316, a bearing protrusion 318, and a hook 320 (seen in FIG. 4C). The orientation of the arch wire slot 308 within the base 302 is substantially parallel to the bonding platform 306. This orientation facilitates insertion of the arch wire 110 when the bracket 300 is bonded to a second upper molar.

Figure 5A:
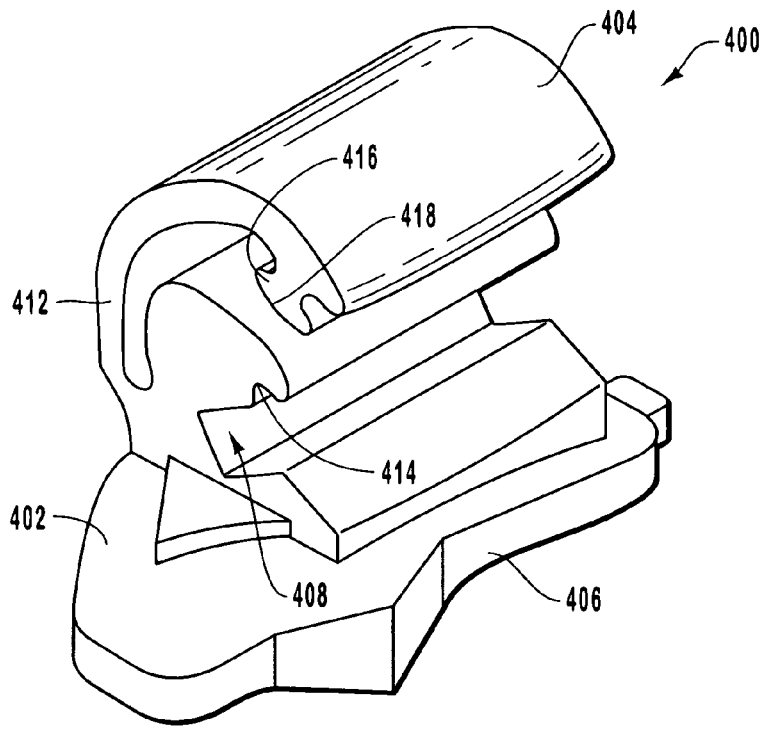
FIGS. 5A-5C illustrate an additional exemplary molar orthodontic bracket according to the invention.
Figure 5B:
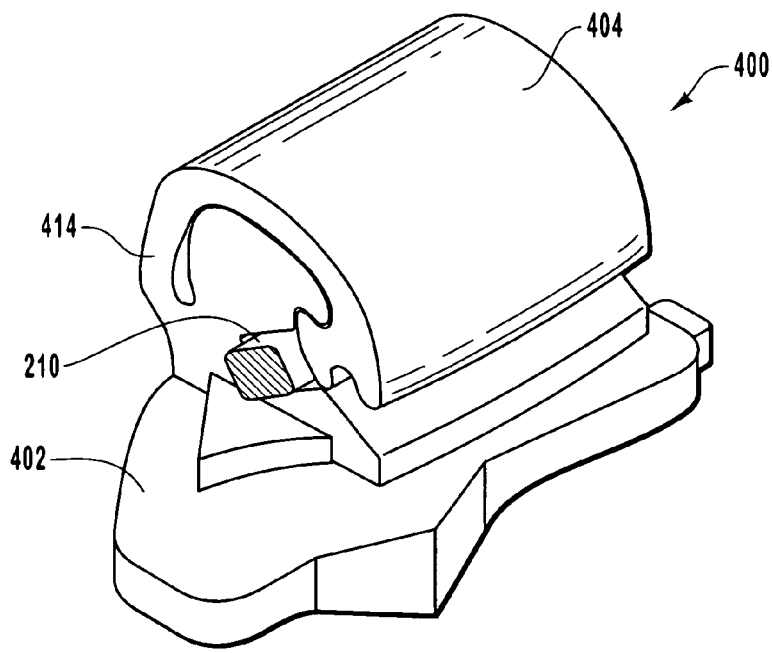
Figure 5C:
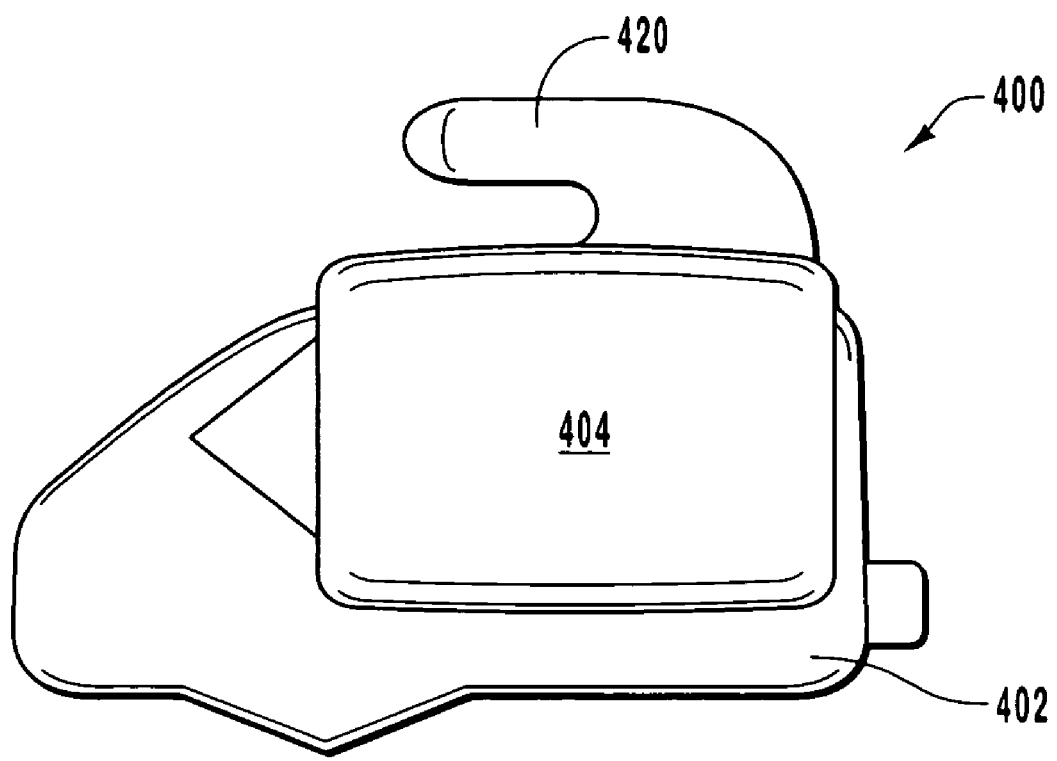

FIGS. 5A-5C illustrate another exemplary embodiment of a molar orthodontic bracket according to the present invention. The bracket 400 is especially configured for placement on the second lower molars, although it may be used on other molars, as desired. The bracket 400 includes a bracket base 402, a ligation cover 404, a bonding platform 406, an arch wire slot 408, an elongate film hinge 412, an angled keyway 414, a locking tongue 416, a bearing protrusion 418, and a hook 420 (seen in FIG. 5C). The orientation of the arch wire slot 408 within the base 402 is angled in toward the tooth. This orientation facilitates insertion of the arch wire 210 when the bracket 400 is bonded to a second lower molar.

Figure 6A:
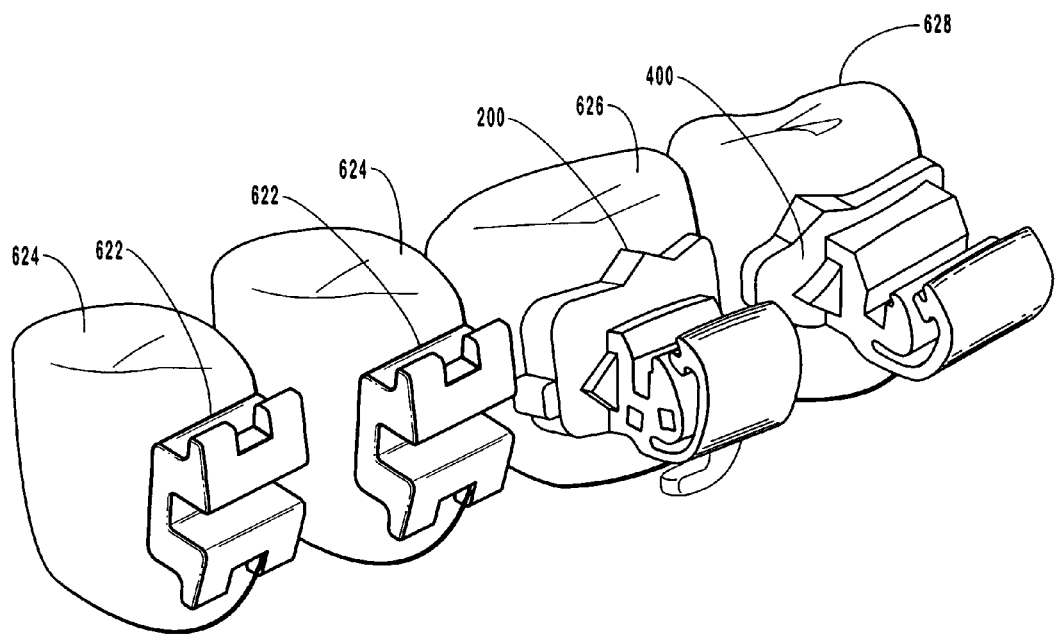
FIG. 6A illustrates a plurality of conventional orthodontic brackets used in combination with the molar orthodontic brackets shown in FIGS. 3A and 5A, each bracket being positioned on a respective tooth.
Figure 6B:
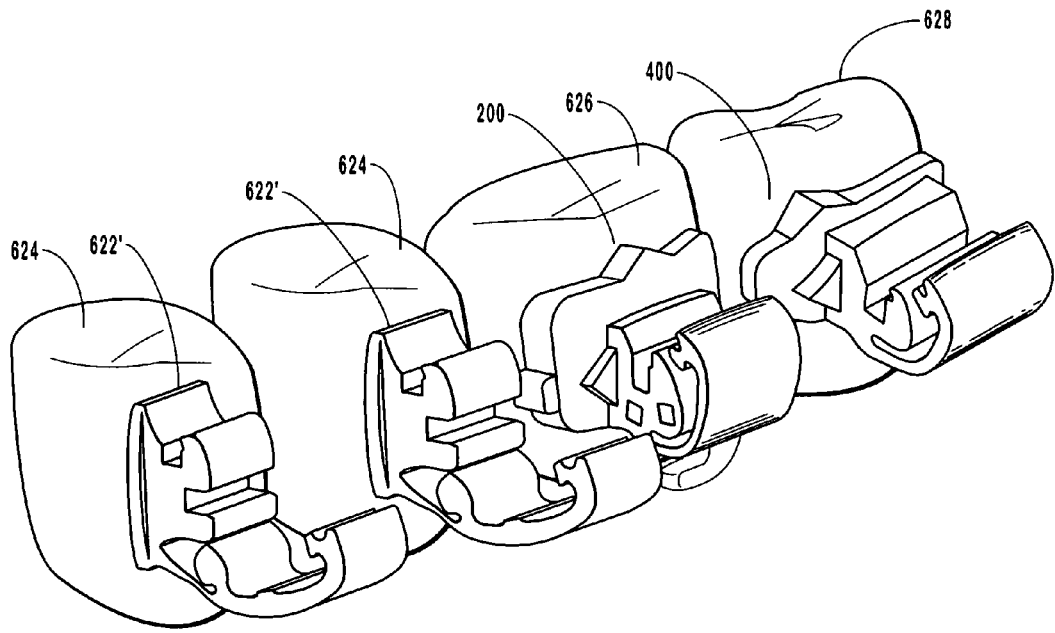
FIG. 6B illustrates a plurality of non-molar self-ligating orthodontic brackets in combination with the molar orthodontic brackets shown in FIGS. 3A and 5A, each bracket being positioned on a respective tooth.

FIGS. 6A-6B illustrate how the molar brackets function in conjunction with non-molar brackets 622 placed on a person's teeth 624. Molar brackets 200 and 400 are positioned on the labial surface of first and second molars 626 and 628, respectively, while one non-molar bracket 622 is positioned on each tooth 624 to be straightened. The non-molar brackets 622 may be non-self-ligating conventional brackets 622 (see FIG. 6A) or self-ligating brackets 622' (see FIG. 6B), as desired.

Figure 7:
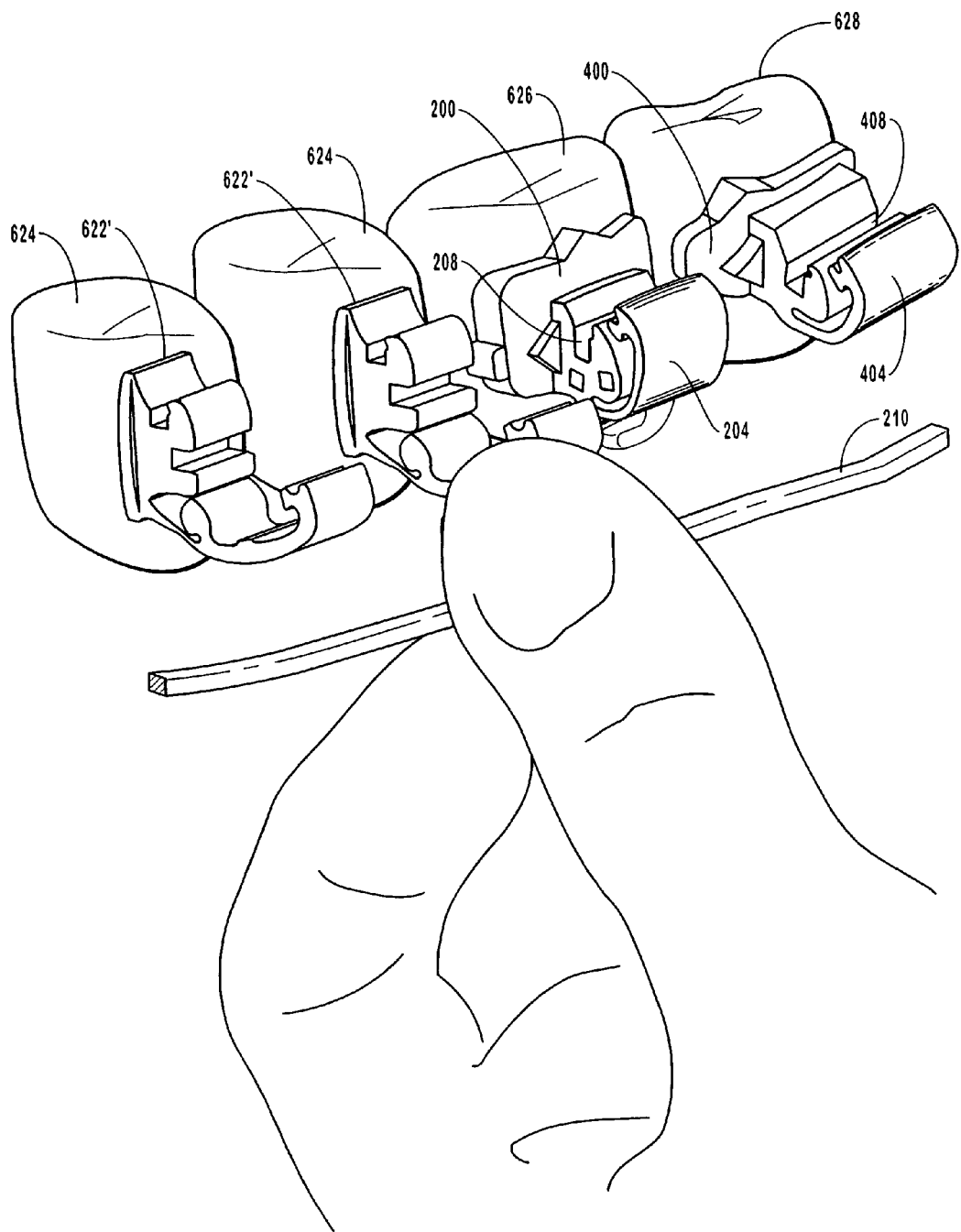
FIG. 7 illustrates insertion of an arch wire into the arch wire slots of two molar orthodontic brackets and a plurality of non-molar self-ligating orthodontic brackets with the ligation covers in an open, non-ligating position.

Referring to FIG. 7, once the brackets have been positioned as desired, an arch wire 210 is inserted into the arch wire slot of each of the brackets. Inserting the arch wire 210 into the molar self-ligating orthodontic brackets 200 and 400 is much easier than with existing tube brackets because the arch wire 210 can be inserted in the initially open arch wire slots 208 and 408 when the ligation covers 204 and 404 are open, rather than feeding them through narrow tunnels. In addition, the arch wire slots of molar brackets 200 and 400 illustrated in FIG. 7 are completely non-occluded by their respective ligation covers (e.g., no portion of the ligation covers remains directly over their respective arch wire slots when in the open position shown in FIG. 7).

Figure 8:
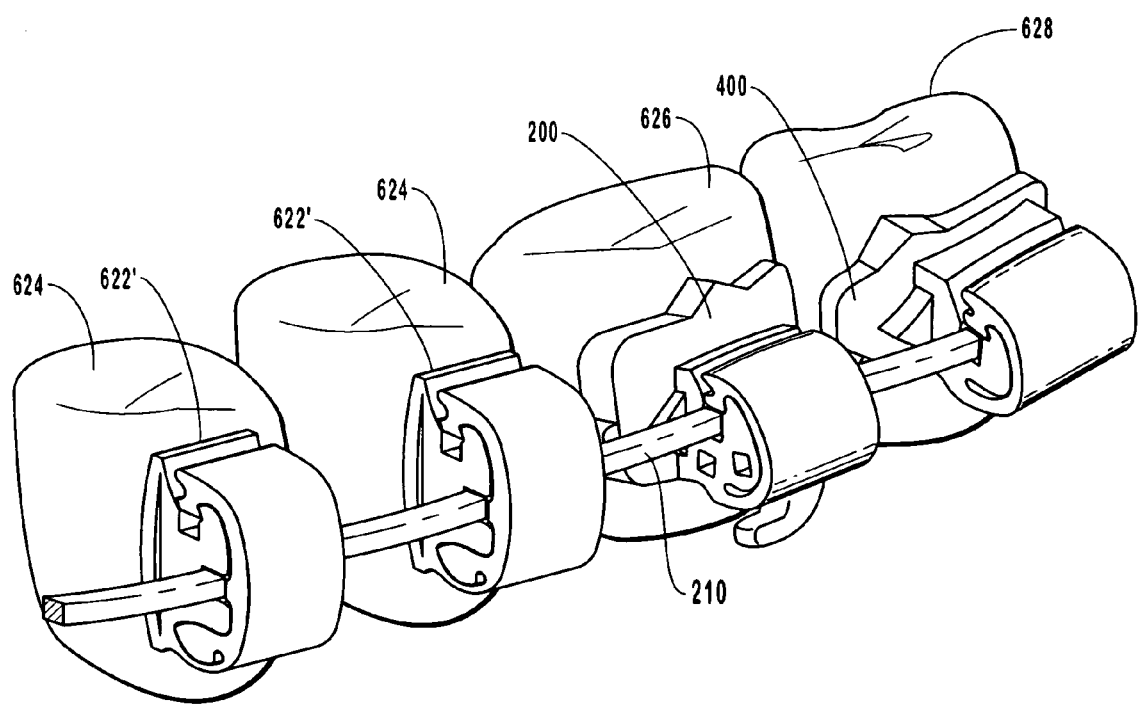
FIG. 8 illustrates the brackets of FIG. 7 with the arch wire in place and the ligation covers in a closed, ligating position.

Referring to FIG. 8, once the arch wire 210 is inserted into each arch wire slot, the ligation covers of molar brackets 200 and 400 are moved and locked in the closed, ligating position in order to retain the arch wire 210 within the arch wire slots of the molar brackets 200 and 400. In order to retain the arch wire within the arch wire slots of self-ligating non-molar brackets 622', the ligation covers are closed. When using conventional non-molar brackets 622 (as seen in FIG. 6A), ligatures may be fitted as known in the art to retain the arch wire 210 within each arch wire slot.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. An orthodontic bracket having dimensions and strength so as to be suitable for use as a molar bracket in combination with a plurality of non-molar brackets in retaining an arch wire during an orthodontic procedure, the orthodontic bracket comprising:
   a bracket base comprised of:
      a bonding platform that is sized and shaped for attachment to a person's molar; and
      a raised portion extending buccally from the bonding platform, the raised portion having an occlusal-gingival width and a mesial-distal length that is at least about 125% of its occlusal-gingival width, the raised portion being attached to the bonding platform across its entire mesial-distal length and occlusal-gingival width, the raised portion having a continuous rounded buccal surface with no slot or other opening interrupting the buccal surface;
   a single arch wire slot disposed in the raised portion of the bracket base and having a distal arch wire receiving opening that is oriented so as to generally point gingivally-occlusally relative to a tooth to which the orthodontic bracket is attached;
   a ligation cover hingedly attached to the bracket base, the ligation cover being selectively movable about a hinge between an open, non-ligating position, in which the arch wire slot is open and completely non-occluded by the ligation cover, and a closed, ligating position relative to the arch wire slot,
the ligation cover wrapping around, covering and having continuous contact with the continuous rounded buccal surface of the raised portion when in the closed, ligating position so as to form a smooth, rounded and continuous top surface of the bracket,
wherein the ligation cover has an occlusal-gingival width and a mesial-distal length that is at least about 125% of its occlusal-gingival width; and
a latch mechanism for selectively locking the ligation cover in the closed, ligating position, the latch mechanism including:
an indentation in a lip of the bracket base that extends distally beyond the distal arch wire receiving opening; and
a locking tongue that extends laterally from an end of the ligation cover and which includes a protrusion configured to mate with the indentation in the lip of the bracket base.

2. An orthodontic bracket as recited in claim 1, wherein the ligation cover is hingedly attached to the bracket base by an integral film hinge comprising a localized region of reduced cross-sectional thickness such that the orthodontic bracket is integrally formed together as a single piece.

3. An orthodontic bracket as recited in claim 2, wherein the orthodontic bracket is molded as a single piece of plastic.

4. An orthodontic bracket as recited in claim 1, wherein the indentation in the lip of the bracket base forms an angled keyway within the archwire slot disposed mesially-distally along a side of the bracket base opposite to where the ligation cover is hingedly attached to the bracket base into which the locking tongue is inserted when the ligation cover is in the closed, ligating position, wherein the locking tongue is disposed mesially-distally along the end of the ligation cover opposite to where the ligation cover is hingedly attached to the bracket base.

5. An orthodontic bracket as recited in claim 1, an end of the ligation cover including a bearing protrusion that extends toward the arch wire slot when the ligation cover is in the closed, ligating position.

6. An orthodontic bracket as recited in claim 1, further including a hook for securing one end of a class II elastic.

7. An orthodontic bracket as recited in claim 1, wherein the mesial-distal length of at least one of the raised portion or ligation cover is at least about 150% of its occlusal-gingival width.

8. An orthodontic bracket as recited in claim 1, wherein the mesial-distal length of at least one of the raised portion or ligation cover is at least about 200% of its occlusal-gingival width.

9. An orthodontic bracket as recited in claim 1, wherein the bonding platform has a mesial-distal length that is at least about 125% of its occlusal-gingival width.

10. An orthodontic bracket as recited in claim 1, wherein the arch wire slot is oriented so that it points substantially vertically when the bracket is placed on a molar during use.

11. An orthodontic bracket as recited in claim 1, wherein the arch wire slot is angled relative to a tooth surface to which the bracket is attached so as to include an opening that partially points away from a tooth to which the orthodontic bracket is attached during use while still generally pointing gingivally-occlusally.

12. A kit for use in providing orthodontic treatment to a plurality of differently-sized and shaped teeth, comprising:
a plurality of orthodontic brackets, at least one of the orthodontic brackets comprising a self-ligating buccal molar bracket and at least one other of the orthodontic brackets comprising a non-molar buccal bracket, the non-molar buccal bracket including an archwire slot that is oriented ligually-bucally, the self-ligating molar bracket having a mesial-distal length that is greater than the mesial-distal length of the non-molar bracket, the molar bracket comprising:
a bracket base comprised of:
a bonding platform that is sized and shaped for attachment to a person's molar; and
a raised portion extending buccally from the bonding platform, the raised portion having an occlusal-gingival width and a mesial-distal length that is at least about 125% of its occlusal-gingival width, the raised portion being attached to the bonding platform across its entire mesial-distal length and occlusal-gingival width, the raised portion having a continuous buccal surface with no slot or other opening interrupting the buccal surface;
an arch wire slot disposed in the raised portion of the bracket base and having a distal arch wire receiving opening that is oriented so as to point toward the occlusal surface of the tooth to which it is attached;
a ligation cover hingedly attached to the bracket base, the ligation cover being selectively movable about a hinge between an open, non-ligating position, in which no portion of the ligation cover remains directly over the arch wire slot, and a closed, ligating position relative to the arch wire slot,
the ligation cover wrapping around, covering and having contact with the buccal surface of the raised portion when in the closed, ligating position so as to form a smooth, rounded and continuous top surface of the bracket,
wherein the ligation cover has an occlusal-gingival width and a mesial-distal length that is at least about 125% of its occlusal-gingival width; and
a latch mechanism for selectively locking the ligation cover in the closed, ligating position, the latch mechanism including:
an indentation in a lip of the bracket base that extends distally beyond the distal arch wire receiving opening: and
a locking tongue that extends laterally from an end of the ligation cover and which includes a protrusion configured to mate with the indentation in the lip of the bracket base.

13. A kit as recited in claim 12, wherein the kit includes a first self-ligating molar bracket configured for placement on a first buccal molar and a second self-ligating molar bracket configured for placement on a second buccal molar.

14. A kit as recited in claim 12, the kit comprising at least one non-self-ligating non-molar bracket.

15. A kit as recited in claim 12, wherein said kit comprises at least one self-ligating non-molar bracket.

16. An orthodontic bracket having dimensions and strength so as to be suitable for use as a molar bracket in combination with a plurality of non-molar brackets in retaining an arch wire during an orthodontic procedure, the orthodontic bracket comprising:
a bracket base comprised of:
a bonding platform that is sized and shaped for attachment to a person's molar; and
a raised portion extending buccally from the bonding platform, the raised portion having an occlusal-gingival width and a mesial-distal length that is at least about 150% of its occlusal-gingival width, the raised portion being attached to the bonding platform across its entire mesial-distal length and occlusal-gingival width, the raised portion having a continuous buccal surface with no slot or other opening interrupting the buccal surface;

an arch wire slot disposed in the raised portion of the bracket base and having a distal arch wire receiving opening that is oriented so as to generally point gingivally-occlusally relative to a tooth to which it is attached;

at least one auxiliary tunnel disposed through said bracket base; and a ligation cover hingedly attached to the bracket base, the ligation cover being selectively movable about a hinge between an open, non-ligating position, in which the arch wire slot is open and completely non-occluded by the ligation cover, and a closed, ligating position relative to the arch wire slot, the ligation cover wrapping around, covering and having contact with the buccal surface of the raised portion when in the closed, ligating position so as to form a smooth, rounded and continuous top surface, wherein the ligation cover has an occlusal-gingival width and a mesial-distal length that is at least about 150% of its occlusal-gingival width.

17. An orthodontic bracket having dimensions and strength so as to be suitable for use as a molar bracket in combination with a plurality of non-molar brackets in retaining an arch wire during an orthodontic procedure, the orthodontic bracket comprising:

a bracket base comprised of:

a bonding platform that is sized and shaped for attachment to a person's molar; and a raised portion extending buccally from the bonding platform, the raised portion having an occlusal-gingival width and a mesial-distal length that is at least about 200% of its occlusal-gingival width, the raised portion being attached to the bonding platform across its entire mesial-distal length and occlusal-gingival width, the raised portion having a continuous buccal surface with no slot or other opening interrupting the buccal surface;

a single arch wire slot disposed in the raised portion of the bracket base and having a distal arch wire receiving opening that is oriented so as to generally point gingivally-occlusally relative to a tooth to which it is attached; and a ligation cover hingedly attached to the bracket base by an integral film hinge comprising a localized region of reduced cross-sectional thickness such that the orthodontic bracket is integrally formed together as a single piece, the ligation cover being selectively movable about the film hinge between an open, non-ligating position, in which no portion of the ligation cover remains directly over the arch wire slot, and a closed, ligating position relative to the arch wire slot, the ligation cover wrapping around, covering and having continuous contact with the continuous rounded buccal surface of the raised portion when in the closed, ligating position so as to form a smooth, rounded and continuous top surface of the bracket, wherein the ligation cover has an occlusal-gingival width and a mesial-distal length that is at least about 200% of its occlusal-gingival width, wherein the integral film hinge does not bias the ligation cover so as to entirely occlude the arch wire slot.

* * * * *

UNITED STATES PATENT AND TRADEMARK OFFICE
CERTIFICATE OF CORRECTION

PATENT NO. : 7,396,230 B2  
APPLICATION NO. : 10/836074  
DATED : July 8, 2008  
INVENTOR(S) : Norbert Abels et al.

Page 1 of 1

It is certified that error appears in the above-identified patent and that said Letters Patent is hereby corrected as shown below:

<u>Figure 5B</u>  
Change reference "414" to read -- 412 --

<u>Column 4</u>  
Line 47, change "10" to -- 100 --

<u>Column 8</u>  
Line 45, change ":" to -- ; --

Signed and Sealed this

Twenty-second Day of December, 2009

David J. Kappos  
*Director of the United States Patent and Trademark Office*